US012208057B2

(12) United States Patent
Adedipe et al.

(10) Patent No.: US 12,208,057 B2
(45) Date of Patent: Jan. 28, 2025

(54) SYSTEM AND METHOD OF NONINVASIVE BLOOD FLOW MEASUREMENT DURING CARDIOPULMONARY RESUSCITATION USING SIGNAL GATING

(71) Applicants: University of Washington, Seattle, WA (US); University of Pittsburgh—Of the Commonwealth System of Higher Education, Pittsburgh, PA (US)

(72) Inventors: Adeyinka Adedipe, Seattle, WA (US); Graham Nichol, Seattle, WA (US); Pierre D. Mourad, Seattle, WA (US); David Salcido, Seattle, WA (US); John Kucewicz, Seattle, WA (US); Matthew Sundermann, Seattle, WA (US)

(73) Assignees: University of Washington, Seattle, WA (US); University of Pittsburgh—Of the Commonwealth System or Higher Education, Pittsburgh, PA (US)

( * ) Notice: Subject to any disclaimer, the term of this patent is extended or adjusted under 35 U.S.C. 154(b) by 1101 days.

(21) Appl. No.: 16/597,656

(22) Filed: Oct. 9, 2019

(65) Prior Publication Data

US 2020/0107989 A1 Apr. 9, 2020

Related U.S. Application Data

(60) Provisional application No. 62/743,435, filed on Oct. 9, 2018.

(51) Int. Cl.
*A61H 31/00* (2006.01)
*A61B 5/00* (2006.01)
(Continued)

(52) U.S. Cl.
CPC ......... *A61H 31/006* (2013.01); *A61B 5/0261* (2013.01); *A61B 5/0295* (2013.01);
(Continued)

(58) Field of Classification Search
None
See application file for complete search history.

(56) References Cited

U.S. PATENT DOCUMENTS

2006/0211942 A1 9/2006 Hoctor et al.
2006/0241459 A1 10/2006 Tai
(Continued)

FOREIGN PATENT DOCUMENTS

WO 2011135288 A2 11/2011

OTHER PUBLICATIONS

Ting, H. H. et al. "Vitamin C improves endothelium-dependent vasodilation in patients with non-insulin-dependent diabetes mellitus" The Journal of Clinical Investigation 1996;97(1):22-28.
(Continued)

*Primary Examiner* — Serkan Akar
(74) *Attorney, Agent, or Firm* — Christensen O'Connor Johnson Kindness PLLC

(57) ABSTRACT

In some embodiments, a blood flow sensor device such as a non-invasive cardiac arrest monitor (NICAM) that uses ultrasound to detect blood flow is used to monitor blood flow during cardiopulmonary resuscitation. One or more gating signal generation devices transmit gating signals to a blood flow monitoring computing device. The blood flow monitoring computing device uses the gating signals to determine time periods during which blood flow information generated by the blood flow sensor device is most likely to be accurate. The blood flow monitoring computing device measures blood flow during the time periods. In some embodiments, the blood flow monitoring computing device presents the measured blood flow to a user. In some embodiments, the blood flow monitoring computing device transmits a command to a chest compression device based on the measured blood flow.

10 Claims, 6 Drawing Sheets

(51) Int. Cl.
*A61B 5/026* (2006.01)
*A61B 5/0295* (2006.01)
*A61B 5/08* (2006.01)
*A61B 8/00* (2006.01)
*A61B 8/06* (2006.01)
*A61B 8/08* (2006.01)

(52) U.S. Cl.
CPC ............ *A61B 5/082* (2013.01); *A61B 5/7271* (2013.01); *A61B 8/06* (2013.01); *A61B 8/4272* (2013.01); *A61B 8/5215* (2013.01); *A61H 2201/501* (2013.01); *A61H 2230/255* (2013.01); *A61H 2230/405* (2013.01)

(56) References Cited

U.S. PATENT DOCUMENTS

| | | | | |
|---|---|---|---|---|
| 2009/0143655 | A1* | 6/2009 | Shani | A61B 5/441 600/323 |
| 2010/0022886 | A1* | 1/2010 | Ayati | A61B 5/6822 600/454 |
| 2010/0076315 | A1 | 3/2010 | Erkamp et al. | |
| 2010/0114220 | A1* | 5/2010 | Paradis | A61H 31/006 601/41 |
| 2010/0275690 | A1 | 11/2010 | Wrobel | |
| 2011/0301513 | A1* | 12/2011 | Freeman | A61H 31/007 600/509 |
| 2012/0184854 | A1 | 7/2012 | Raju et al. | |
| 2013/0282069 | A1* | 10/2013 | Thiagarajan | A61N 1/3993 607/3 |
| 2015/0289838 | A1 | 10/2015 | Nichol et al. | |
| 2017/0332995 | A1* | 11/2017 | Eibl | A61B 8/4281 |
| 2019/0008720 | A1* | 1/2019 | Joshi | A61G 7/018 |

OTHER PUBLICATIONS

Vaillancourt, Christian et al. "The impact of increased chest compression fraction on return of spontaneous circulation for out-of-hospital cardiac arrest patients not in ventricular fibrillation" Resuscitation 82 (2011) 1501-1507.

Voelckel, Wolfgang G. et al. "Effects of Active Compression-Decompression Cardiopulmonary Resuscitation with the Inspiratory Threshold Valve in a Young Porcine Model of Cardiac Arrest" Pediatric Research, vol. 51, No. 4, 2002, pp. 523-527.

Wakeling, H. G. et al. "Intraoperative oesophageal Doppler guided fluid management shortens postoperative hospital stay after major bowel surgery" British Journal of Anaesthesia 95 (5): 634-642.

Wang, Chonghe et al. "Monitoring of the central blood pressure waveform via a conformal ultrasonic device" Nature Biomedical Engineering, Sep. 2018; 2(9): 687-695.

Wilber, David J. et al. "Out-of-Hospital Cardiac Arrest: Use of Electrophysiologic Testing in the Prediction of Long-Term Outcome" The New England Journal of Medicine, vol. 318, No. 1, pp. 19-24.

Kanthos, Theodoros et al. "Baseline Hemodynamics in Anesthetized Landrace-Large White Swine: Reference Values for Research in Cardiac Arrest and Cardiopulmonary Resuscitation Models" Journal of the American Association for Laboratory Animal Science, vol. 46, No. 5, Sep. 2007, pp. 21-25.

Yelderman, Mark L. et al. "Continuous Thermodilution Cardiac Output Measurement in Intensive Care Unit Patients" Journal of Cardiothoracic and Vascular Anesthesia, vol. 6, No. 3, Jun. 1992, pp. 270-274.

Yellon, Derek M. et al. "Myocardial Reperfusion Injury" The New England Journal of Medicine, Sep. 13, 2007, 357;11, pp. 1121-1135.

Yu, Alfred C. H. et al. "An Automated Carotid Pulse Assessment Approach Using Doppler Ultrasound" IEEE Transactions on Biomedical Engineering, vol. 55, No. 3, Mar. 2008, pp. 1072-1081.

Adedipe, Adeyinka A. et al. "Carotid Doppler blood flow measurement during cardiopulmonary resuscitation is feasible: A first in man study" Resuscitation 96 (2015) pp. 121-125.

Adrie, Christophe et al. "Successful Cardiopulmonary Resuscitation After Cardiac Arrest as a "Sepsis-Like" Syndrome" American Heart Association, Circulation May 10, 2002; 106:562-568.

Aichinger, Gernot et al. "Cardiac Movement Identified on Prehospital Echocardiography Predicts Outcome in Cardiac Arrest Patients" Prehospital Emergency Care, Jan. 11, 2012, 16:2, pp. 251-255, DOI: 10.3109/10903127.2011.640414.

Allan, R. B. et al. "A Comparison of Flow-mediated Dilatation and Peripheral Artery Tonometry for Measurement of Endothelial Function in Healthy Individuals and Patients with Peripheral Arterial Disease" European Journal of Vascular and Endovascular Surgery, 45(3) Mar. 2013, pp. 263-269.

Anderson, Travis, et al. "Preconditioning and the oxidants of sudden death" Current Opinion in Critical Care, 2003, 9:194-198.

Arbeille, Philippe, "Doppler Sensors and Harnesses for Cardiac and Peripheral Arterial Flow Monitoring" Ultrasound in Medicine & Biology, 23(3), 1997, pp. 415-423.

Arheden, Håkan, "Left-to-Right Cardiac Shunts: Comparison of Measurements Obtained with MR Velocity Mapping and with Radionuclide Angiography" Radiology, May 1999, pp. 453-458.

Berg, Robert A. et al. "Association Between Diastolic Blood Pressure During Pediatric In-Hospital Cardiopulmonary Resuscitation and Survival" Circulation. 2018; 137:1784-1795. DOI: 10.1161/CIRCULATIONAHA. 117.032270.

Bernstein, Donald P. "Impedance cardiography: Pulsatile blood flow and the biophysical and electrodynamic basis for the stroke vol. equations" Journal of Electrical Bioimpedance, vol. 1, pp. 2-17, 2010.

Bernstein, D. P. "Limitations of Impedance Cardiography" Obesity Surgery, 15, 2005, pp. 659-660.

Bernstein, D. P. "Stroke volume equation for impedance cardiography" Medical and Biological Engineering and Computing 2005, vol. 43, pp. 443-450.

Binanay, Cynthia "Evaluation Study of Congestive Heart Failure and Pulmonary Artery Catheterization Effectiveness" Journal of the American Medical Association, Oct. 5, 2005, vol. 294, No. 13, pp. 1625-1633.

Böttiger, Bernd W. et al. "Activation of Blood Coagulation After Cardiac Arrest is not Balanced Adequately by Activation of Endogenous Fibrinolysis" Nov. 1, 1995 | http://doi.org/10.116/01.CIR.92.9.2572 | Circulation. 1995:92:2572-2578.

Callaway, Clifton W. et al. "Waveform analysis of ventricular fibrillation to predict defibrillation" Current Opinion in Critical Care, 2005, 11:192-199.

Chan, Paul S. et al. "Delayed Time to Defibrillation after In-Hospital Cardiac Arrest" The New England Journal of Medicine, 358(1), Jan. 3, 2008, pp. 9-17.

Chaney, John C. et al. "Minimally invasive hemodynamic monitoring for the intensivitst: Current and emerging technology" Critical Care Medicine, 2002; 30:2338-2345.

Chang, Wei-Tien et al. "Postresuscitation myocardial dysfunction: correlated factors and prognostic implications" Intensive Care Medicine, 2007; 33:88-95 DOI 10.1007/s00134-006-0442-9.

Chen, Qun et al. "Production of Reactive Oxygen Species by Mitochondria" Journal of Biological Chemistry, vol. 278, No. 38, Sep. 19, 2003, pp. 36027-36031.

Cheskes, Sheldon et al. "The impact of peri-shock pause on survival from out-of-hospital shockable cardiac arrest during the Resuscitation Outcomes Consortium PRIMED trial" Resuscitation 85 (2014) 336-342.

Cheskes, Sheldon et al. "Perishock Pause an Independent Predictor of Survival From Out-of-Hospital Shockable Cardiac Arrest" Circulation. 2011; 124:58-66.

Christenson, Jim et al. "Chest Compression Fraction Determines Survival in Patients With Out-of-Hospital Ventricular Fibrillation" Circulation. 2009; 120: 1241-1247.

Corretti, Mary C. "Guidelines for the Ultrasound Assessment of Endothelial-Dependent Flow-Mediated Vasodilation of the Brachial Artery" Journal of the American College of Cardiology, vol. 39, No. 2, 2002, pp. 257-265.

(56) References Cited

OTHER PUBLICATIONS

Creager, Mark A. et al. "Impaired vasodilation of forearm resistance vessels in hypercholesterolemic humans" The Journal of Clinical Investigation, 1990; 86(1): 228-234. https://doi.org/10.1172/JCI114688.

De Roos, Nicole M. et al. "Within-Subject Variability of Flow-Mediated Vasodilation of the Brachial Artery in Healthy Men and Women: Implications for Experimental Studies" Ultrasound in Medicine and Biology, vol. 29, No. 3, 2003, pp. 401-406.

Deanfield, John et al. "Endothelial function and dysfunction. Part I: Methodological issues for assessment in the different vascular beds: A statement by the Working Group on Endothelin and Endothelial Factors of the European Society of Hypertension" Journal of Hypertension 2005, vol. 23, No. 1, pp. 7-17.

Eberle, B. et al. "Checking the carotid pulse check: diagnostic accuracy of first responders in patients with and without a pulse" Resuscitation 33 (1996) pp. 107-116.

Fellahi, Jean-Luc et al. "Noninvasive Assessment of Cardiac Index in Healthy Volunteers: A Comparison Between Thoracic Impedance Cardiography and Doppler Echocardiography" Anesthesia and Analgesia, vol. 108, No. 5, May 2009, pp. 1553-1559.

Fibrinolytic Therapy Trialists' Collaborative Group "Indications for fibrinolytic therapy in suspected acute myocardia Infarction: collaborative overview of early mortality and major morbidity results from all randomised trials of more than 1000 patients" Lancet 1994; 343: 311-322.

Fink, Katrin et al. "Severe endothelial injury and subsequent repair in patients after successful cardiopulmonary resuscitation" Critical Care 2010 14:R104, 11 pages.

Friess, Stuart H. et al. "Hemodynamic Directed Cardiopulmonary Resuscitation Improves Short-Term Survival From Ventricular Fibrillation Cardiac Arrest" Critical Care Medicine, Dec. 2013, vol. 41, No. 12, pp. 2698-2704.

Friess, Stuart H. et al. "Hemodynamic directed CPR improves cerebral perfusion pressure and brain tissue oxygenation" Resuscitation 85 (2014) pp. 1298-1303.

Gando, Satoshi et al. "Massive Fibrin Formation with Consecutive Impairment of Fibrinolysis in Patients with Out-of- Hospital Cardiac Arrest" Thrombosis and Haemostasis, vol. 77, No. 2, Feb. 1997, pp. 278-282.

Garcia, Solange C. et al. "Independency of myocardial stunning of endothelial stunning?" Basic Research in Cardiology, vol. 102, No. 4 (2007), pp. 359-367.

Garcia, Oliveira et al. "Prognostic Value of Endothelial Function in Patients with Atherosclerosis: Systematic Review" Arquivos brasileiros de cardiologia, 2012; 99(3); pp. 857-864.

Go, Alan S. et al. "Heart Disease and Stroke Statistics—2013 Update: A Report from the American Heart Association", Circulation. 2013;127:e6-e245.

Grotti, S. et al. "Endothelium, ischemia and the good side of oxygen free radicals" Clinical Hemorheology and Microcirculation 39 (2008) pp. 197-203.

Hamilton, Timothy T. et al. "PulseCO: A Less-Invasive Method to Monitor Cardiac Output From Arterial Pressure After Cardiac Surgery" The Annals of Thoracic Surgery, 2002;74:S1408-1412.

Harris, Ryan A. et al. "Ultrasound Assessment of Flow-Mediated Dilation" Hypertension. May 2010;55:1075-1085.

Higashi, Yukihito, et al. "Regular Aerobic Exercise Augments Endothelium-Dependent Vascular Relaxation in Normotensive as Well as Hypertensive Subjects: Role of Endothelium-Derived Nitric Oxide: Role of Endothelium-Derived Nitric Oxide" Circulation. 1999; 100:1194-1202.

Hightower, David, et al. "Decay in Quality of Closed-Chest Compressions Over Time" Annals of Emergency Medicine, Sep. 1995, 26:3, pp. 300-303.

Hostler, David et al. "Effect of real-time feedback during cardiopulmonary resuscitation outside hospital: prospective, cluster-randomised trial" BMJ 2011;342:d512, doi:10.1136/bmj.d512. 10 pages.

Huet, Olivier et al. "Postresuscitation syndrome: Potential role of hydroxyl radical-induced endothelial cell damage" Critical Care Medicine 2011 vol. 39, No. 7, pp. 1712-1720.

Idei, Naomi et al. "A novel noninvasive and simple method for assessment of endothelial function: Enclosed zone flow-mediated vasodilation (ezFMD) using an oscillation amplitude measurement" Atherosclerosis 229 (2013) pp. 324-330.

Idris, Ahamed H. et al. "Relationship Between Chest Compression Rates and Outcomes From Cardiac Arrest" Circulation. 2012;125:3004-3012.

Irace, Concetta et al. "Comparison of endothelial function evaluated by strain gauge plethysmography and brachial artery ultrasound" Atherosclerosis 158 (2001) pp. 53-59.

Kanahara, Masaaki, et al. "New Methodological Approach to Improve Reproducibility of Brachial Artery Flow-Mediated Dilatation" Echocardiography 2014;31:197-202.

Kern, Karl B. et al. "Myocardial Perfusion Pressure: A Predictor of 24-Hour Survival During Prolonged Cardiac Arrest in Dogs" Resuscitation 16 (1988) pp. 241-250.

Khan, Akbar H. et al. "Prognostic Implication of Early Ejection Fraction on Long-Term Mortality and Quality of Life Following Out-of-Hospital Cardiac Arrest" The American Journal of Cardiology vol. 93, Apr. 15, 2004, pp. 1027-1030.

Kucewicz, John C. et al. "Towards a non-invasive cardiac arrest monitor: An in vivo pilot study" Resuscitation 134 (2019) pp. 76-80.

Kuehne, T. et al. "Magnetic resonance imaging guided catheterisation for assessment of pulmonary vascular resistance: in vivo validation and clinical application in patients with pulmonary hypertension" Heart 2005;91:1064-1069. doi:10.1136/hrt.2004.038265.

Kurita, T. et al. "Comparison of the accuracy of the lithium dilution technique with the thermodilution technique for measurement of cardiac output" British Journal of Anaesthesia 1997;79:770-775.

Lapostolle, Frederic, et al. "Basic Cardiac Life Support Providers Checking the Carotid Pulse: Performance, Degree of Conviction, and Influencing Factors" Academic Emergency Medicine 2004; 11:878-880.

Larabee, Todd M. et al. "A novel hands-free carotid ultrasound detects low-flow cardiac output in a swine model of pulseless electrical activity arrest" The American Journal of Emergency Medicine (2001) 29; 1141-1146.

Laurent, Ivan et al. "High-Volume Hemofiltration After Out-of-Hospital Cardiac Arrest" Journal of the American College of Cardiology, vol. 46, No. 3, 2005, pp. 432-437.

Laurent, Ivan et al. "Reversible Myocardial Dysfunction in Survivors of Out-of-Hospital Cardiac Arrest" Journal of the American College of Cardiology, vol. 40, No. 12, 2002, pp. 2110-2116.

Lefer, David J. et al. "Oxidative Stress and Cardiac Disease" The American Journal of Medicine, Sep. 2000; 109:315-323.

Lindberg, Lars et al. "The effects of epinephrine/norepinephrine on end-tidal carbon dioxide concentration, coronary perfusion pressure and pulmonary arterial blood flow during cardiopulmonary resuscitation" Resuscitation 43 (2000) pp. 129-140.

Linder, Lilly, et al. "Indirect Evidence for Release of Endothelium-Derived Relaxing Factor in Human Forearm Circulation In Vivo: Blunted Response in Essential Hypertension" Circulation 1990;81:1762-1767.

Linton, R. A. et al. "Cardiac output measured by lithium dilution and transpulmonary thermodilution in patients in a paediatric intensive care unit" Intensive Care Medicine (2000) 26:1507-1511.

Linton, Robert, et al. "Lithium dilution cardiac output measurement: A comparison with thermodilution" Critical Care Medicine, Nov. 1997, vol. 25, Issue 11, 11 pages.

Lurie, Keith G. et al. "Improving Active Compression-Decompression Cardiopulmonary Resuscitation With an Inspiratory Impedance Valve" Circulation. 1995;91:1629-1632.

Marqué, Sophie, et al. "Comparison between Flotrac-Vigileo and Bioreactance, a totally noninvansive method for cardiac output monitoring" Critical Care 2009, 13:R73 (doi:10.1186/cc7884) 6 pages.

McFall, M. R. et al. "The use of oesophageal Doppler cardiac output measurement to optimize fluid management during colorectal surgery" European Journal of Anaesthesiology, 2004, 21: 571-583.

(56) References Cited

OTHER PUBLICATIONS

McNamara, Robert L. et al. "Effect of Door-to-Balloon Time on Mortality in Patients With ST-Segment Elevation Myocardial Infarction" Journal of the American College of Cardiology, vol. 47, No. 11, 2006, pp. 2180-2186.

McVeigh, G. E. et al. "Impaired endothelium-dependent and independent vasodilation in patients with Type 2 (non-Insulin-dependent) diabetes mellitus" Diabetologia (1992) 35:771-776.

Meaney, Peter A. et al. "Cardiopulmonary Resuscitation Quality: Improving Cardiac Resuscitation Outcomes Both Inside and Outside the Hospital: A Consensus Statement From the American Heart Association" Circulation. 2013;128:417-435.

Merchant, Raina M. et al. "Incidence of treated cardiac arrest in hospitalized patients in the United States" Critical Care Medicine, vol. 39, No. 11, 2011, pp. 2401-2406.

Minei, Joseph P. et al. "Severe Traumatic Injury: Regional Variation in Incidence and Outcome" Annals of Surgery, vol. 252, No. 1, Jul. 2010, pp. 149-157.

Moule, Pam, "Checking the carotid pulse: diagnostic accuracy in students of the healthcare professions" Resuscitation 44 (2000) 195-201.

Mozaffarian, Dariush et al. "Heart Disease and Stroke Statistics-2015 Update: A Report From the American Heart Association" Circulation. 2015;131:e29-e322.

Nadkarni, Vinay M. et al. "First Documented Rhythm and clinical Outcome From In-Hospital Cardiac Arrest Among Children and Adults" Journal of the American Medical Association, Jan. 4, 2006, vol. 295, No. 1, pgs.

Negovsky, Vladimir A. "Postresuscitation disease" Critical Care Medicine, Oct. 1988, vol. 16, No. 10. pp. 942-946.

Neumar, Robert W. et al. "Part 8: Adult Advanced Cardiovascular Life Support: 2010 American Heart Association Guidelines for Cardiopulmonary Resuscitation and Emergency Cardiovascular Care" Circulation. 2010; 122[suppl3]: S729-S767.

Neumar, Robert W. et al. "Post-Cardiac Arrest Syndrome: Epidemiology, Pathophysiology, Treatment, and Prognostication" Circulation. 2008;118:2452-2483.

Nichol, Graham et al. "A Cumulative Meta-Analysis of the Effectiveness of Defibrillator-Capable Emergency Medical Services for Victims of Out-of-Hospital Cardiac Arrest" Annals of Emergency Medicine, Oct. 1999;34:517-525.

Nichol, Graham et al. "Regional Variation in Out-of-Hospital Cardiac Arrest Incidence and Outcome" Journal of the American Medical Association, Sep. 24, 2008, vol. 300, No. 12, pp. 1423-1431.

Niemann, James T. et al. "Outcome of out-of-hospital postcountershock asystole and pulseless electrical activity versus primary asystole and pulseless electrical activity" Critical Care Medicine, 2001, vol. 29, No. 12, pp. 2366-2370.

Nolan, J. P. et al. "Therapeutic Hypothermia After Cardiac Arrest: An Advisory Statement by the Advanced Life Support Task Force of the International Liaison Committee on Resuscitation" Circulation. 2003; 108:118-121.

Ochoa, F. Javier et al. "The effect of rescuer fatigue on the quality of chest compressions" Resuscitation 37 (1998) 149-152.

Panza, Julio A. et al. "Abnormal Endothelium-Dependent Vascular Relaxation in Patients with Essential Hypertension" The New England Journal of Medicine Jul. 5, 1990, vol. 323 No. 1, pp. 22-27.

Paradis, Norman A. et al. "Coronary Perfusion Pressure and the Return of Spontaneous Circulation in Human Cardiopulmonary Resuscitation" Journal of the American Medical Association, Feb. 23, 1990, vol. 263, No. 8, pp. 1106-1113.

Peberdy, Mary Ann et al. "Cardiopulmonary resuscitation of adults in the hospital: A report of 14720 cardiac arrests from the National Registry of Cardiopulmonary Resuscitation" Resuscitation 58 (2003) 297-308.

Raval, Nirav Y. et al. "Multicenter Evaluation of Noninvasive Cardiac Output Measurement by Bioreactive Technique" Journal of Clinical Monitoring and Computing (2008) 22:113-119.

Razavi, Reza et al. "Cardiac catheterisation guided by MRI in children and adults with congenital heart disease" Lancet Dec. 6, 2003, vol. 362, pp. 1877-1882.

Risdal, Martin et al. "Automatic Identification of Return of Spontaneous Circulation During Cardiopulmonary Resuscitation" IEEE Transactions on Biomedical Engineering, vol. 55, No. 1, Jan. 2008, pp. 60-68.

Roger, Véronique L. et al. "Heart Disease and Stroke Statistics-2011 Update: A Report From the American Heart Association" Circulation. Feb. 1, 2011; 123(4): e18-e209. doi:10.1161/CIR. 0b013e3182009701.

Sanders, Arthur B. et al. "End-Tidal Carbon Dioxide Monitoring During Cardiopulmonary Resuscitation: A Prognostic Indicator for Survival" Journal of the American Medical Association, Sep. 8, 1989, vol. 262, No. 10, pp. 1347-1351.

Sanders, Arthur B. et al. "Expired PCO2 as an Index of Coronary Perfusion Pressure" American Journal of Emergency Medicine, Mar. 1985, vol. 3, No. 2, pp. 147-149.

Sanders, Arthur B. et al. "Expired PCO2 as a Prognostic Indicator of Successful Resuscitation From Cardiac Arrest" Annals of Emergency Medicine, 14:Oct. 10, 1985, pp. 948-952.

Sasson, Comilla et al. "Predictors of Survival From Out-of-Hospital Cardiac Arrest: A Systematic Review and Meta-Analysis" Circulation: Cardiovascular Quality and Outcomes. 2010;63-81.

Schultz, Jason et al. "Sodium nitroprusside enhanced cardiopulmonary resuscitation (SNPeCPR) improves vital organ perfusion pressures and carotid blood flow in a porcine model of cardiac arrest" Resuscitation 83 (2012) 374-377.

Shah, Monica R. et al. "Impact of the Pulmonary Artery Catheter in Critically Ill Patients: Meta-analysis of Randomized Clinical Trials" Journal of the American Medical Association, Oct. 5, 2005, vol. 294, No. 13, pp. 1664-1670.

Shoemaker, Willie C. et al. "Noninvasive Hemodynamic Monitoring for Combat Casualties" Military Medicine, vol. 171, Sep. 2006, pp. 813-820.

Squara, Pierre et al. "Noninvasive cardiac output monitoring (NICOM): a clinical validation" Intensive Care Medicine (2007) 33:1191-1194.

Stiell, Ian G. et al. "What is the Optimal Chest Compression Depth During Out-of-Hospital Cardiac Arrest Resuscitation of Adult Patients?" Circulation. 2014; 130:1962-1970.

Stoner, Lee et al. "How should flow-mediated dilation be normalized to its stimulus?" Clinical Physiology and Functional Imaging (2013) 33, pp. 75-78.

Stover, John F. et al. "Noninvasive cardiac output and blood pressure monitoring cannot replace an invasive monitoring system in critically ill patients" BMC Anesthesiology 2009, 9:6, 5 pages.

Sutton, Robert M. et al. "Hemodynamic-directed cardiopulmonary resuscitation during in-hospital cardiac arrest" Resuscitation 85 (2014) 983-986.

Taddei, Stefano et al. "Vitamin C Improves Endothelium-Dependent Vasodilation by Restoring Nitric Oxide Activity in Essential Hypertension" Circulation. 1998;97:2222-2229.

Takase, Bonpei et al. "Comparable Prognostic Value of Vasodilator Response to Acetylcholine in Brachial and Coronary Arteries for Predicting Long-Term Cardiovascular Events in Suspected Coronary Artery Disease" Circulation Journal, Jan. 2006, vol. 70, pp. 49-56.

\* cited by examiner

SYSTEM AND METHOD OF NONINVASIVE BLOOD FLOW MEASUREMENT DURING CARDIOPULMONARY RESUSCITATION USING SIGNAL GATING

CROSS-REFERENCE(S) TO RELATED APPLICATION(S)

This application claims the benefit of Provisional Application No. 62/743,435, filed Oct. 9, 2018, the entire disclosure of which is hereby incorporated by reference in its entirety for all purposes.

BACKGROUND

Time-sensitive emergency conditions including traumatic injury, myocardial infarction, and out-of-hospital cardiac arrest (OHCA) are collectively the leading cause of death in the United States. The five-fold variation in survival after OHCA between communities suggests that many patients can be successfully treated if the presence of cardiac arrest is identified early enough after its onset and subsequent treatment is optimized.

Rapid and accurate manual assessment of the presence or absence of blood flow during cardiac arrest has been used to determine the need for cardiopulmonary resuscitation (CPR) by attempting to palpate over a major artery (e.g. carotid or femoral) for the presence, absence, or quality of a pulse. Unfortunately, lay persons and emergency personnel experience difficulty assessing this accurately. As a consequence of these limitations of manual assessment, potentially lifesaving CPR may be withheld from those individuals not recognized to be in cardiac arrest.

Importantly, greater blood flow as measured by invasive monitors in major vessels during attempted resuscitation from cardiac arrest is associated with greater likelihood of survival in animals and humans. However, interruptions of CPR such as to apply or use monitoring techniques are associated with decreased survival. It is plausible that real-time feedback guided by monitors to improve processes of care during attempted resuscitation could improve survival. Importantly, experience to date with such feedback has been mixed in part because the measures of blood flow use are inexact.

Thus there is a large need for an accurate non-invasive blood flow monitoring device that can be rapidly applied to subjects not in cardiac arrest to identify the onset of arrest, or to someone who is unconscious or not responding to verify the presence or absence of cardiac arrest, or to someone who is known to be in cardiac arrest to guide the adequacy of attempted resuscitation as well as to assess prognosis.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a system for measuring blood flow during cardiopulmonary resuscitation of a subject is provided. The system comprises a blood flow sensor device, a gating signal generation device, and a blood flow monitoring computing device. The blood flow monitoring computing device includes at least one processor and a non-transitory computer-readable medium having computer-executable instructions stored thereon that, in response to execution by the at least one processor, cause the blood flow monitoring computing device to perform actions. The actions comprise receiving blood flow information from the blood flow sensor device; receiving gating information from the gating signal generation device; determining time periods for sampling the blood flow information based on the gating information; and measuring blood flow indicated by the blood flow information during the time periods.

In some embodiments, a computer-implemented method of measuring blood flow during cardiopulmonary resuscitation of a subject is provided. A computing device receives blood flow information from a blood flow sensor device. The computing device receives gating information from a gating signal generation device. The computing device determines time periods for sampling the blood flow information based on the gating information. The computing device measures blood flow indicated by the blood flow information during the time periods.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Recently ultrasound was used to measure the velocity of carotid blood flow in animals and humans that were in cardiac arrest. Carotid blood flow correlates with end-tidal $CO_2$, coronary perfusion pressure and initial response to treatment. An advantage of measuring carotid blood flow using ultrasound is that is can be readily applied to a patient without interfering with the resuscitation field (i.e. chest). A disadvantage of early approaches to carotid ultrasound during resuscitation is that they require manual localization of the artery on the neck, which can delay visualization of flow or disrupt treatment.

We previously proposed a non-invasive cardiac arrest monitor (NICAM), which uses imaging or non-imaging ultrasound to measure blood flow during CPR. NICAM was described in PCT Publication No. WO2014066859A1, the entire disclosure of which is hereby incorporated by reference herein for all purposes. Our approach provides blood flow measurement via a form factor that addresses the problems with use of standard ultrasound systems. The NICAM ultrasound probe is integrated with a flexible adhesive pad with preprinted anatomic cues to enable attaching and maintaining the sensor on the skin over a major artery. NICAM measures blood flow velocity and other properties of blood flow during chest compressions and interprets the height and width of the velocity signal to guide and improve the quality of chest compressions.

Animal experiments have revealed that the performance of NICAM is inhibited by motion artifacts associated with CPR. Embodiments of the present disclosure improve the accuracy of NICAM blood flow measurements around compression artifacts. By gating the blood velocity measurements of NICAM simultaneously to another physiologic signal, blood flow measurements are improved. We also present another blood flow signal obtained via near-infrared spectroscopy (NIRS), which provides information about tissue perfusion, to measure the adequacy of blood flow during CPR.

Figure 1:
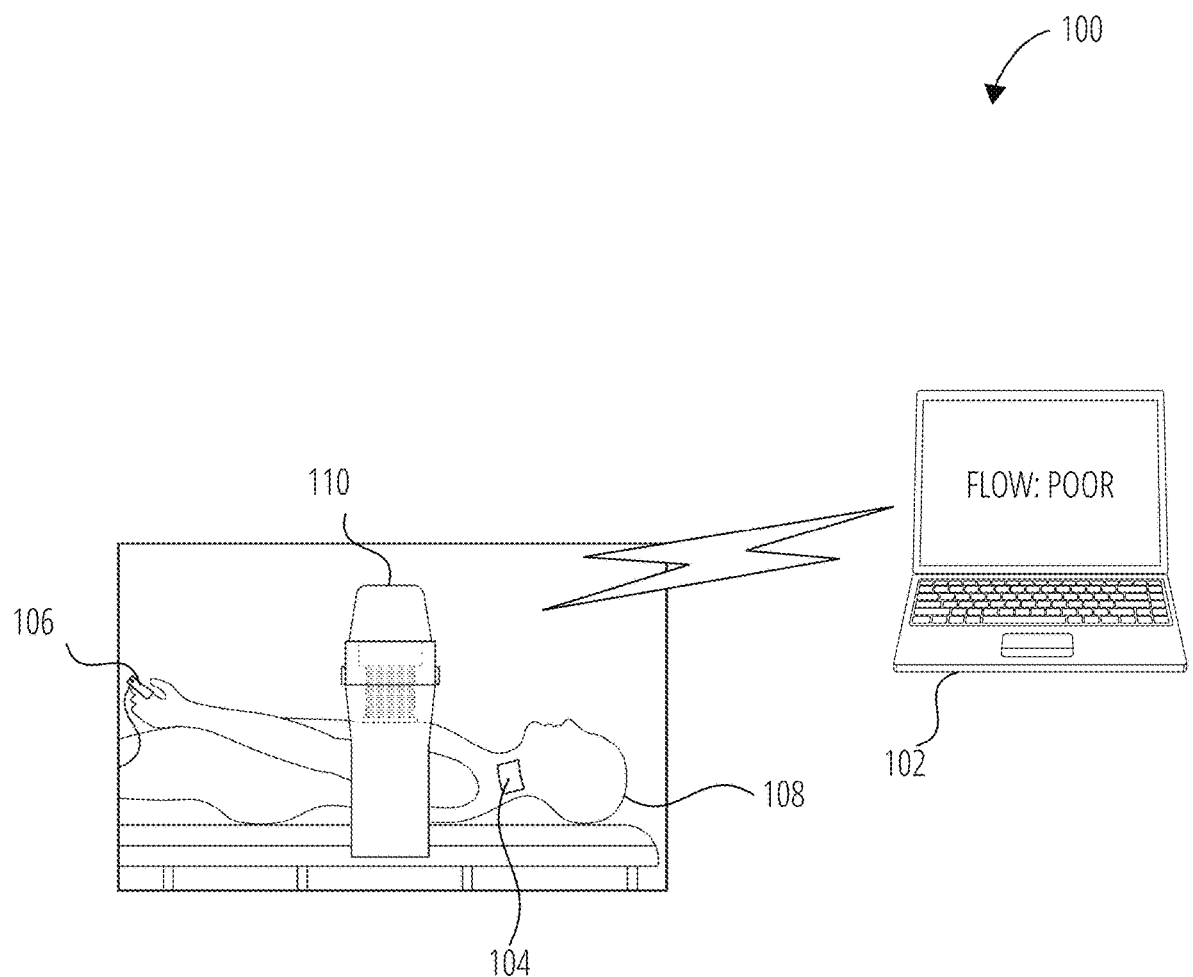
FIG. 1 is a schematic diagram that illustrates a non-limiting example embodiment of a system for monitoring blood flow during cardiopulmonary resuscitation according to various aspects of the present disclosure.

FIG. 1 is a schematic illustration of a system 100 for monitoring blood flow during cardiopulmonary resuscitation (CPR) according to various aspects of the present disclosure. As shown, a subject 108 is experiencing a cardiac incident for which CPR is appropriate. As shown, an automatic chest compression device 110 has been coupled to the subject 108. The chest compression device 110 is configured to automatically apply forceful compressions to the chest of the subject 108 in order to circulate blood to the brain and other organs in the absence of effective cardiac activity. Though a chest compression device 110 is illustrated in FIG. 1, in some embodiments, the technology described herein may be used alongside manual CPR administration.

In addition to the chest compression device 110, a NICAM sensor device 104 has also been attached to the subject 108. As illustrated, the NICAM sensor device 104 includes an ultrasound probe that is configured to measure blood flow within the carotid artery, and has been affixed via an adhesive patch to the neck of the subject 108. In some embodiments, the NICAM sensor device 104 may be configured to measure blood flow within a different blood vessel, including but not limited to a femoral artery. In some embodiments, the adhesive patch of the NICAM sensor device 104 may include markings to help guide accurate placement of the NICAM sensor device 104 in an emergency situation.

As shown, an NIRS sensor device 106 has also been attached to the subject 108. The NIRS sensor device 106 includes an infrared sensor that measures tissue perfusion at a peripheral location, such as a finger. The NIRS sensor device 106 is an example of a gating signal generation device, as will be described further below.

During operation, the NICAM sensor device 104 and NIRS sensor device 106 transmit information to a blood flow monitoring computing device 102. In some embodiments, the NICAM sensor device 104 and/or NIRS sensor device 106 are communicatively coupled to the blood flow monitoring computing device 102 via any type of communication technology, including but not limited to a wireless network (including but not limited to an Ethernet network, a USB network, and/or a FireWire network) and/or a wireless network (including but not limited to a 2G, 3G, 4G, 5G, LTE, Wi-Fi, WiMAX, and/or Bluetooth network). The blood flow monitoring computing device 102 receives the information, and uses the blood flow information received from the NICAM sensor device 104 along with gating information received from the NIRS sensor device 106 to determine accurate blood flow measurements for the subject 108. By using the gating information, the blood flow monitoring computing device 102 can compensate for motion artifacts and thereby provide accurate information to be used to help improve the administration of CPR in order to improve patient outcomes.

Figure 2:
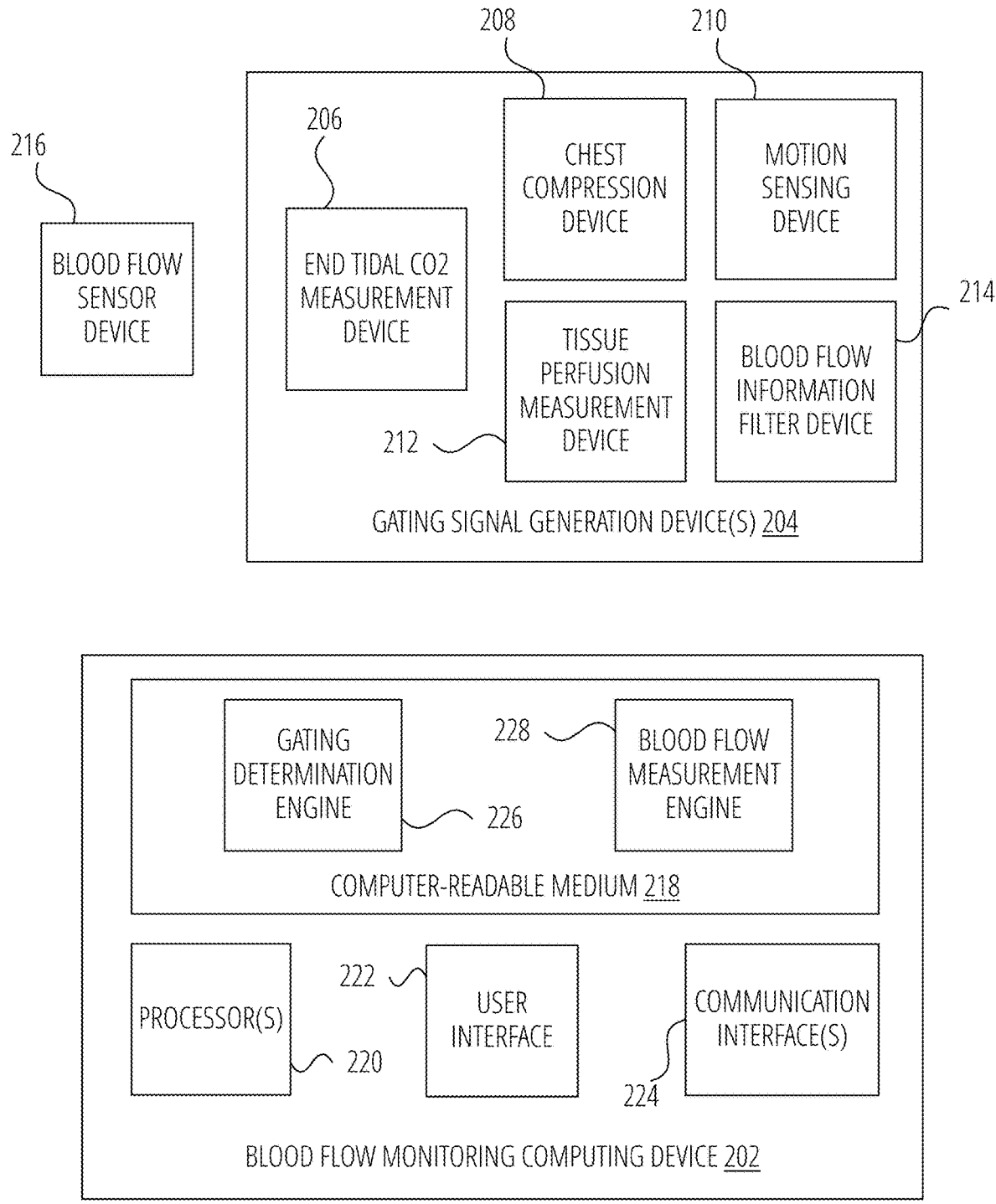
FIG. 2 is a block diagram that illustrates non-limiting example embodiments of a blood flow sensor device, a set of potential gating signal generation devices, and a blood flow monitoring computing device according to various aspects of the present disclosure.

FIG. 2 is a block diagram that illustrates non-limiting example embodiments of a blood flow sensor device, a set of gating signal generation devices, and a blood flow monitoring computing device according to various aspects of the present disclosure. In some embodiments, the blood flow sensor device 216 and at least one gating signal generation device 204 transmit information to the blood flow monitoring computing device 202 via any suitable networking technology. The blood flow monitoring computing device 202 uses the information from the gating signal generation device 204 to determine time periods during which the information from the blood flow sensor device 216 is most likely to accurately represent the blood flow of the subject 108. The blood flow monitoring computing device 202 then analyzes the information from the blood flow sensor device 216 during those time periods to measure the blood flow.

Though FIG. 2 illustrates the blood flow sensor device 216, the gating signal generation device 204, and the blood flow monitoring computing device 202 as separate devices, in some embodiments, two or more of these devices may be combined into a single device. For example, the components and functionality of the blood flow monitoring computing device 202 and the blood flow sensor device 216 may be combined into a single device.

In some embodiments, the blood flow sensor device 216 includes an ultrasound probe that, when aimed toward a blood vessel from a position on the skin over the blood vessel, can detect the motion of blood within the blood vessel. The detected motion can be translated into a flow rate, a flow direction, or other values. In some embodiments, the ultrasound probe is positioned on the subject 108 using an adhesive pad. In some embodiments, the adhesive pad may include markings that help correctly position the ultrasound probe with respect to the blood vessel. One non-limiting example of such a marking is an indicator of an expected location of an anatomical landmark. In some embodiments, the blood flow sensor device 216 is provided by the NICAM sensor device described in the international patent publication incorporated by reference above. In other embodiments, any other suitable device may be used as the blood flow sensor device 216.

Several examples of gating signal generation devices 204 are shown. The illustrated examples are an end tidal CO2 measurement device 206, a chest compression device 208, a motion sensing device 210, a tissue perfusion measurement device 212, and a blood flow information filter device 214. FIG. 2 illustrates multiple gating signal generation devices 204 to show multiple different types of gating signal generation device 204, though in some embodiments, only a single type of gating signal generation device 204 may be present in a given embodiment.

In some embodiments, the end tidal CO2 measurement device 206 is any suitable device for measuring an end-tidal CO2 (ETCO2) value, including but not limited to a capnometric or capnographic device that is configured to detect CO2 concentrations within the airway of the subject 108. The end tidal CO2 measurement device 206 may be configured to transmit ETCO2 values to the blood flow monitoring computing device 202 for use as a gating signal.

In some embodiments, the chest compression device 208 is an automatic device that is configured to generate cardiopulmonary resuscitation chest compressions while mounted to the subject 108. One non-limiting example of a chest compression device 208 is a LUCAS® chest compression system manufactured by Jolife A B. While the chest compression device 208 may be part of the system 100 as a whole, in some embodiments, the chest compression device 208 may also serve as a gating signal generation device 204 by transmitting compression timing information to the blood flow monitoring computing device 202 for use as a gating signal.

In some embodiments, the motion sensing device 210 is any suitable device for measuring motion, including but not limited to an accelerometer, a gyroscope, an electronic compass, and/or combinations thereof. In some embodiments, the motion sensing device 210 is configured to be placed on the subject 108 in order to detect motion of the subject 108, and to provide the detected motion to the blood flow monitoring computing device 202 as a gating signal.

In some embodiments, the tissue perfusion measurement device 212 is any suitable device for measuring a volume of blood in tissue. In some embodiments, a photoplethysmograph device that uses a near infrared spectroscope, such as a finger plethysmograph, may be used as a tissue perfusion measurement device 212. In some embodiments, the tissue perfusion measurement device 212 may measure other values, including but not limited to an oxygen saturation and/or a pulse. In some embodiments, the tissue perfusion measurement device 212 is configured to provide the information that it collects to the blood flow monitoring computing device 202 for use as a gating signal.

In some embodiments, the blood flow information filter device 214 is a computing device that receives blood flow information from the blood flow sensor device 216. The blood flow information filter device 214 may be configured to process the blood flow information, including but not limited to applying a band-pass filter to signals produced by the blood flow sensor device 216. Signals determined through use of the band-pass filter may be usable to detect the occurrence of chest compressions. Accordingly, the blood flow information filter device 214 may provide the signals to the blood flow monitoring computing device 202 for use as a gating signal.

The gating signal generation devices 204 illustrated in FIG. 2 are examples only, and in some embodiments, different devices may be used. For example, in some embodiments, a transthoracic impedance sensor may be used as a gating signal generation device 204, and transthoracic impedance signals may be used as a gating signal.

In some embodiments, the blood flow monitoring computing device 202 is a laptop computing device, a desktop computing device, a tablet computing device, a mobile computing device, a computing device integrated into a monitor/defibrillator, or any other suitable type of computing device. The blood flow monitoring computing device 202 receives signals from the blood flow sensor device 216 and at least one gating signal generation device 204, and may present measured blood flow information to a user. In some embodiments, the blood flow monitoring computing device 202 may also transmit commands to other devices, such as the chest compression device 208, in response to the measured blood flow information.

As shown, the blood flow monitoring computing device 202 includes a processor 220, a user interface 222, one or more communication interface(s) 224, and a computer-readable medium 218. In some embodiments, the processor 220 may be any suitable type of computing processor that is configured to process computer-executable instructions or other logic stored on the computer-readable medium 218. In some embodiments, the computer-readable medium "Computer-readable medium" refers to a removable or nonremovable device that implements any technology capable of storing information in a volatile or non-volatile manner to be read by a processor of a computing device, including but not limited to: a hard drive; a flash memory; a solid state drive; random-access memory (RAM); read-only memory (ROM); a CD-ROM, a DVD, or other disk storage; a magnetic cassette; a magnetic tape; and a magnetic disk storage.

In some embodiments, the user interface 222 may include a display device configured to present one or more user interface elements. The user interface elements may show components of the measured blood flow information to a user. In some embodiments, the display device may be a flat-screen display, a touch-screen display, or any other suitable type of multi-purpose display device. In some embodiments, the display device may be a multiple-segment display for the sake of simplicity. In some embodiments, the at least one communication interface 224 may include one or more wired communication interfaces (including but not limited to an Ethernet interface, a USB interface, or a FireWire interface) and/or one or more wireless communication interfaces (including but not limited to 2G, 3G, 4G, 5G, LTE, Wi-Fi, WiMAX, or Bluetooth interfaces).

As shown, the computer-readable medium 218 includes a gating determination engine 226 and a blood flow measurement engine 228. In some embodiments, the gating determination engine 226 is configured to receive gating information from at least one gating signal generation device 204, and to use the gating information to determine time periods during which the blood flow information should be sampled. In some embodiments, the blood flow measurement engine 228 analyzes the blood flow information during the time periods in order to determine the measured blood flow. Further details of the actions taken by these components are described below.

Figure 3:
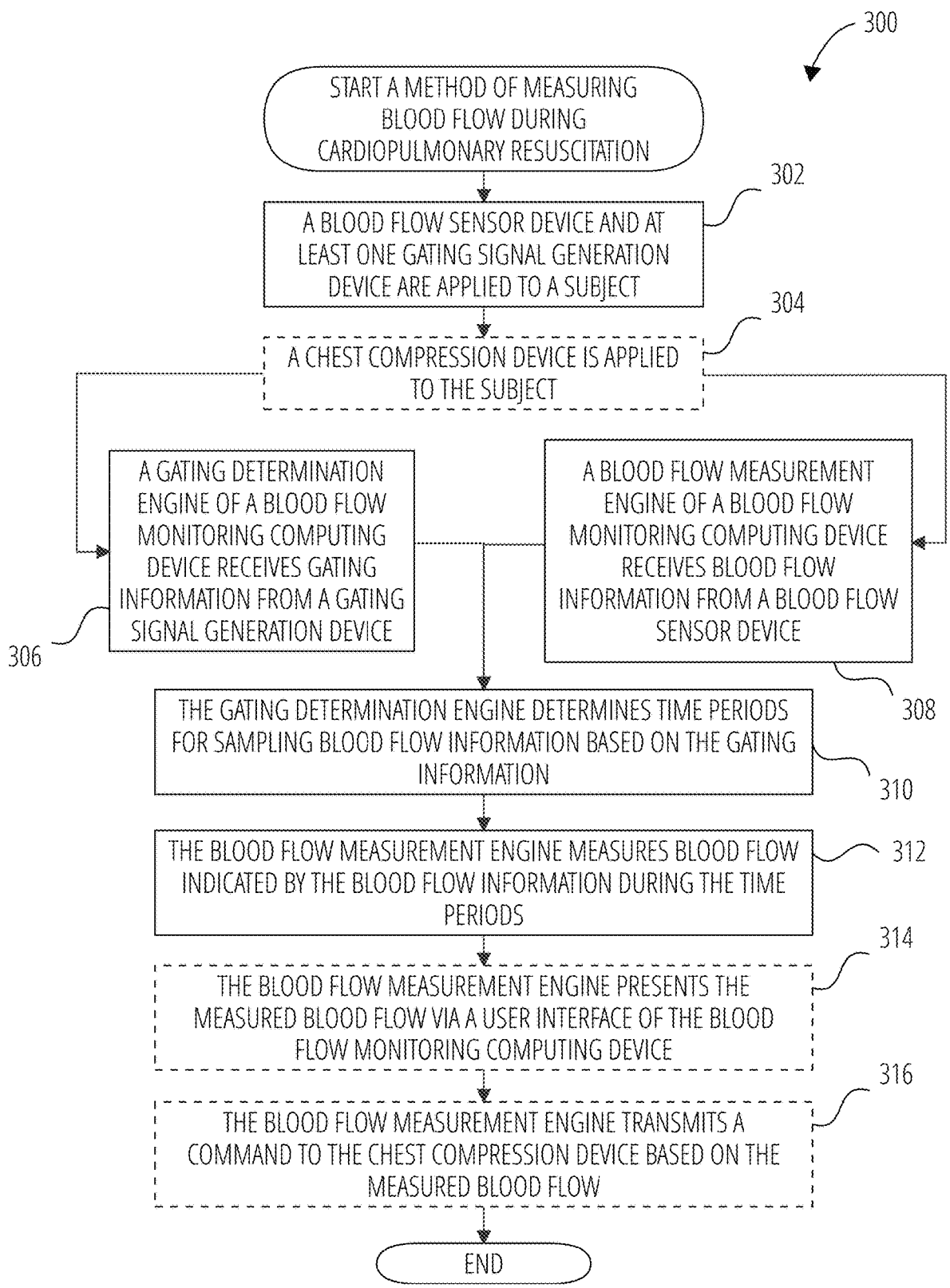
FIG. 3 is a flowchart that illustrates a non-limiting example embodiment of a method of measuring blood flow during cardiopulmonary resuscitation according to various aspects of the present disclosure.

FIG. 3 is a flowchart that illustrates a non-limiting example embodiment of a method of measuring blood flow during cardiopulmonary resuscitation according to various aspects of the present disclosure.

From a start block, the method 300 proceeds to block 302, where a blood flow sensor device 216 and at least one gating signal generation device 204 are applied to a subject 108. In some embodiments, applying the blood flow sensor device 216 may involve positioning an adhesive pad that is associated with an ultrasound probe in an appropriate location, such as over a carotid or femoral artery. Application of the gating signal generation device 204 will depend on the type of gating signal generation device 204 used. As some non-limiting examples, a motion sensing device 210 may include an adhesive pad, clip, elastic band, or other means for attaching the motion sensing device 210 to the subject 108. An end tidal CO2 measurement device 206 may be inserted into an airflow device such as a tracheal tube. A tissue perfusion measurement device 212 may include a clip or strap that allows the device to be coupled to the subject 108. A blood flow information filter device 214 may be communicatively coupled to the blood flow sensor device 216 to receive information therefrom for deriving gating information.

At optional block 304, a chest compression device 208 is applied to a subject 108. In some embodiments, applying the chest compression device 208 to the subject 108 may involve positioning the chest compression device 208 around the chest of the subject 108, and may involve positioning the arms of the subject 108 with respect to the chest compression device 208. Block 304 is illustrated as optional because, in some embodiments, manual chest compressions may be performed instead of using an automatic chest compression device 208.

At block 306, a gating determination engine 226 of a blood flow monitoring computing device 202 receives gating information from a gating signal generation device 204. The type of gating information will depend on the type of gating signal generation device 204 used. For example, an end tidal CO2 measurement device 206 may transmit ETCO2 data, a tissue perfusion measurement device 212 may transmit blood volume and/or oxygen saturation data, a motion sensing device 210 may transmit motion data, a chest compression device 208 may transmit chest compression timing data, and a blood flow information filter device 214 may transmit data filtered from blood flow information.

At block 308, a blood flow measurement engine 228 of a blood flow monitoring computing device 202 receives blood flow information from a blood flow sensor device 216. In some embodiments, the blood flow information indicates speed of the motion of blood within a blood vessel. In some embodiments, the blood flow information may indicate a directionality of the motion of blood within the blood vessel. In some embodiments, the blood flow information may also include motion artifacts that are induced by the chest compression device 208 and/or other movement of the subject 108.

As illustrated, block 306 and block 308 are performed in parallel. Typically, the gating information and the blood flow information are both collected continuously by the gating signal generation device 204 and the blood flow sensor device 216, respectively, throughout execution of the method 300.

At block 310, the gating determination engine 226 determines time periods for sampling blood flow information based on the gating information. The technique used by the gating determination engine 226 to determine the time periods depends on the type of gating signal generation device 204 that is generating the gating information. Once the gating information is generated, it is used to detect time periods during which the blood flow information is least likely to be affected by compression-induced motion artifacts. In some embodiments, the gating determination engine 226 may use a point detected using a technique described below to determine a start time of each time period. The gating determination engine 226 may use the determined point as the start of the time period, or may choose a time that is a predetermined amount of time after the determined point, such as a tenth of a second, as the start of the time period. The gating determination engine 226 may then choose a time that is a predetermined amount of time after the start time, such as a tenth of a second (or about a tenth of a second, such as between 0.09 and 0.11 of a second), to be used as the end of the time period.

Typically, the time periods immediately follow the top and/or the bottom of a compression stroke. Accordingly, each type of gating information may be processed in a different way to detect the top and/or the bottom of the compression strokes, or some other time periods during the compression cycles at which motion artifacts would be least likely to affect the blood flow information.

For example, if the gating signal generation device 204 is a tissue perfusion measurement device 212, the gating determination engine 226 may analyze a waveform transmitted by the tissue perfusion measurement device 212 that represents blood volume in the tissue under the tissue perfusion measurement device 212. The gating determination engine 226 may detect inflection points in the waveform that indicate points where the changes in blood volume transition from increasing to decreasing to determine the start of each time period.

As another example, if the gating signal generation device 204 is a motion sensing device 210, the gating determination engine 226 may analyze indications of motion transmitted by the motion sensing device 210 to detect points with a minimum of motion, and may use those points to determine the start of each time period.

As yet another example, if the gating signal generation device 204 is an end tidal CO2 measurement device 206, the gating determination engine 226 may analyze a waveform transmitted by the end tidal CO2 measurement device 206 that represents the partial pressure of $CO_2$ in the respiratory gasses to find a point between an inhalation and an exhalation. This point may then be used to determine the start of a time period. Chest compressions may also create artifacts in the ETCO2 signal. These artifacts could be detected and used to determine the start of each time period. In some embodiments, the waveform transmitted by the end tidal CO2 measurement device 206 may include a significant temporal offset from the signal from the blood flow sensor device 216, and so the temporal offset would be determined before using the signal from the end tidal CO2 measurement device 206 for gating.

As still another example of a gating signal generation device 204, if the gating signal generation device 204 is a chest compression device 208, then the gating determination engine 226 may analyze the signals transmitted by the chest compression device 208 to find points when the signals indicate the top and/or bottom of the compression strokes occur. These points may then be used to determine the start of time periods.

As a final example of a gating signal generation device 204, if the gating signal generation device 204 is a blood flow information filter device 214, the gating determination engine 226 may analyze a waveform transmitted by the blood flow information filter device 214 that represents background tissue motion that the blood flow information filter device 214 filtered out of the blood flow information. The gating determination engine 226 may detect points at peaks and valleys of the waveform, or, if the waveform represents an absolute value of detected motion, the gating determination engine 226 may detect points where the absolute value of detected motion is zero. Those points may then be used to determine the start of time periods. In some embodiments, instead of using the background tissue motion information directly, the gating determination engine 226 may subtract the background tissue motion from the blood flow information, and may then use the peaks and valleys of the blood flow information itself to determine the points to use to determine the starts of the time periods.

Figure 4:
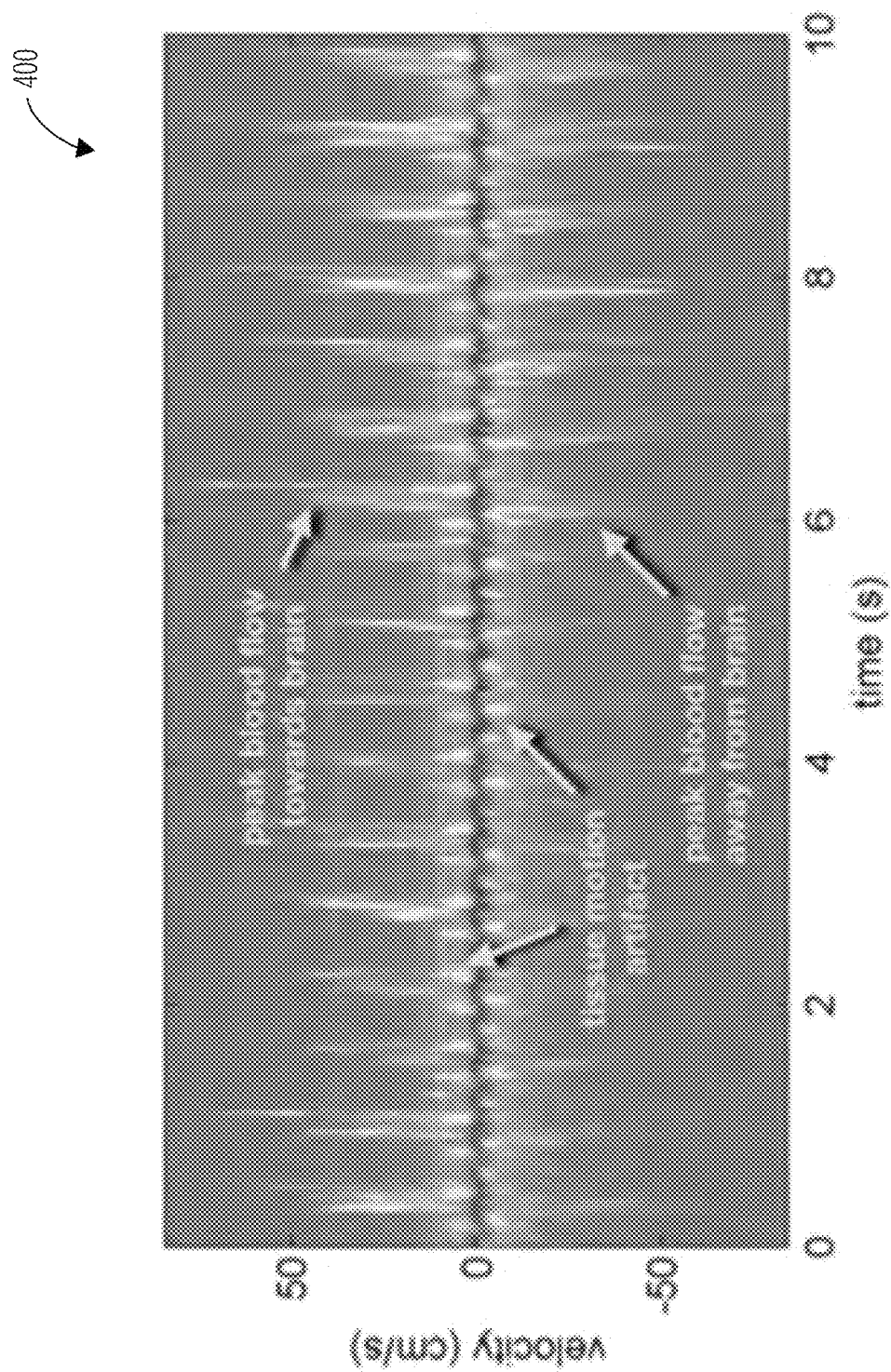
FIG. 4 is a chart that illustrates a non-limiting example embodiment of blood flow information generated by a blood flow sensor device according to various aspects of the present disclosure.
Figure 5:
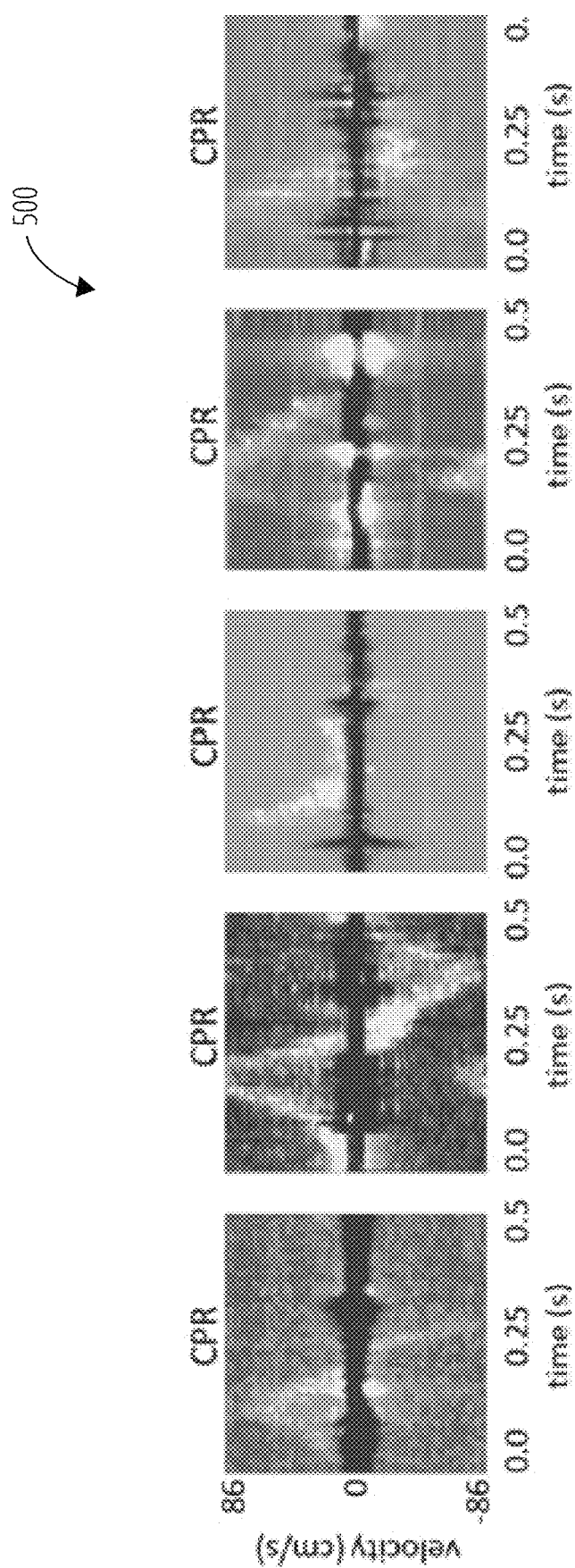
FIG. 5 includes charts that illustrate other non-limiting example embodiments of blood flow information generated by a blood flow sensor device according to various aspects of the present disclosure.

FIG. 4 is a chart that illustrates a non-limiting example embodiment of blood flow information generated by a blood flow sensor device 216 according to various aspects of the present disclosure. The dark, regular waveform near the velocity axis of the chart 400 indicates a signal filtered out by a band pass filter of the blood flow information filter device 214 because it is likely to indicate background tissue motion. Each point where this dark waveform crosses the velocity axis (i.e., each point where the background tissue motion is determined to be zero) may indicate points to use to determine a start of a time period. FIG. 5 includes multiple charts that illustrate other non-limiting example embodiments of blood flow information generated by a blood flow sensor device 216 according to various aspects of the present disclosure. Again, the dark waveforms near the velocity axes of the charts 500 indicate a signal filtered out by a band pass filter of the blood flow information filter device 214 because they are likely to indicate background tissue motion.

Returning to FIG. 3, at block 312, the blood flow measurement engine 228 measures blood flow indicated by the blood flow information during the time periods. In some embodiments, the blood flow measurement engine 228 may use the magnitude of the blood flow indicated by the blood flow information during the time period as the measured blood flow. In some embodiments, the blood flow measurement engine 228 may first filter the blood flow information using the blood flow information filter device 214 to remove background motion values from the blood flow information. In some embodiments, the blood flow measurement engine 228 may also determine a directionality of the blood flow (e.g., away from the head or towards the head).

At optional block 314, the blood flow measurement engine 228 presents the measured blood flow via a user interface 222 of the blood flow monitoring computing device 202. In some embodiments, the blood flow measurement engine 228 may present a numeric value that indicates a flow rate. In some embodiments, the blood flow measurement engine 228 may present a qualitative value (e.g., excellent, good, fair, poor) that represents the measured blood flow. In some embodiments, the blood flow measurement engine 228 may also present the directionality of the measured blood flow. In some embodiments, the user interface 222 may include a display device, and the measured blood flow may be shown via the display device. In some embodiments, the user interface 222 may include a loudspeaker, and the measured blood flow may be presented in an audio format, including but not limited to by synthesized speech, an alarm tone, or an instruction. In some embodiments, the blood flow measurement engine 228 may use the communication interface 224 to transmit the presentation of the measured blood flow to a remote computing device for review by a remote care provider or for storage in a health data record.

At optional block 316, the blood flow measurement engine 228 transmits a command to the chest compression device 208 based on the measured blood flow. In some embodiments, the blood flow measurement engine 228 may determine that changing the rate of compressions, changing the timing between compressions, changing the strength of compressions, or changing some other characteristics of the compressions would improve the blood flow, and the command may cause the chest compression device 208 to implement the changes. In some embodiments, the blood flow measurement engine 228 may determine that the measured blood flow indicates the return of cardiac activity, and so the command may cause the chest compression device 208 to pause compressions. In some embodiments, instead of transmitting a command to the chest compression device 208, a command for changing the compressions (e.g., "rate faster," "rate slower," "press deeper," "stop compressions," etc.) may be generated by a loudspeaker in order to guide manual compressions.

Block 314 and block 316 are illustrated as optional because, in some embodiments, only one of block 314 and block 316 may be performed. In some embodiments, both block 314 and block 316 may be performed.

The method 300 then proceeds to an end block and terminates. The method 300 is illustrated in FIG. 3 as operating a single time and then terminating. However, in some embodiments, the method 300 generally loops back from block 316 to block 306/block 308 to operate continually while cardiopulmonary resuscitation continues.

Figure 6:
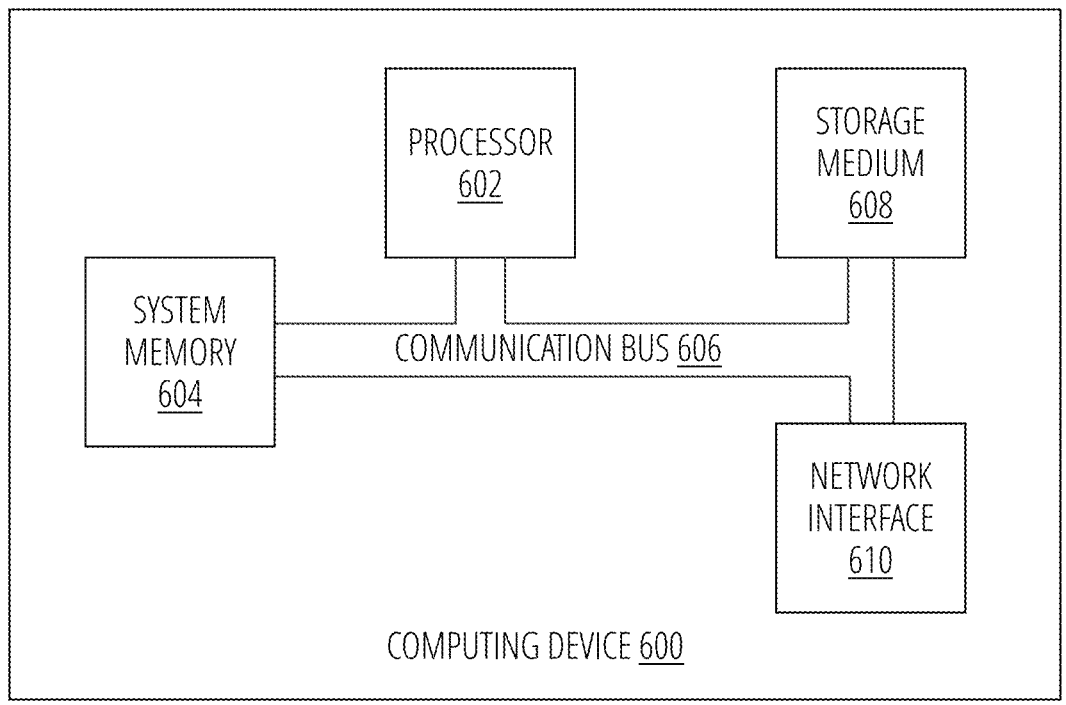
FIG. 6 is a block diagram that illustrates a non-limiting example embodiment of a computing device appropriate for use as a computing device with embodiments of the present disclosure.

FIG. 6 is a block diagram that illustrates aspects of an exemplary computing device 600 appropriate for use as a computing device of the present disclosure. While multiple different types of computing devices were discussed above, the exemplary computing device 600 describes various elements that are common to many different types of computing devices. While FIG. 6 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Some embodiments of a computing device may be implemented in or may include an application-specific integrated circuit (ASIC), a field-programmable gate array (FPGA), or other customized device. Moreover, those of ordinary skill in the art and others will recognize that the computing device 600 may be any one of any number of currently available or yet to be developed devices.

In its most basic configuration, the computing device 600 includes at least one processor 602 and a system memory 604 connected by a communication bus 606. Depending on the exact configuration and type of device, the system memory 604 may be volatile or nonvolatile memory, such as read only memory ("ROM"), random access memory ("RAM"), EEPROM, flash memory, or similar memory technology. Those of ordinary skill in the art and others will recognize that system memory 604 typically stores data and/or program modules that are immediately accessible to and/or currently being operated on by the processor 602. In this regard, the processor 602 may serve as a computational center of the computing device 600 by supporting the execution of instructions.

As further illustrated in FIG. 6, the computing device 600 may include a network interface 610 comprising one or more components for communicating with other devices over a network. Embodiments of the present disclosure may access basic services that utilize the network interface 610 to perform communications using common network protocols. The network interface 610 may also include a wireless network interface configured to communicate via one or more wireless communication protocols, such as Wi-Fi, 2G, 3G, LTE, WiMAX, Bluetooth, Bluetooth low energy, and/or the like. As will be appreciated by one of ordinary skill in the art, the network interface 610 illustrated in FIG. 6 may represent one or more wireless interfaces or physical communication interfaces described and illustrated above with respect to particular components of the computing device 600.

In the exemplary embodiment depicted in FIG. 6, the computing device 600 also includes a storage medium 608. However, services may be accessed using a computing device that does not include means for persisting data to a local storage medium. Therefore, the storage medium 608 depicted in FIG. 6 is represented with a dashed line to indicate that the storage medium 608 is optional. In any event, the storage medium 608 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

Suitable implementations of computing devices that include a processor 602, system memory 604, communication bus 606, storage medium 608, and network interface 610 are known and commercially available. For ease of illustration and because it is not important for an understanding of the claimed subject matter, FIG. 6 does not show some of the typical components of many computing devices. In this regard, the computing device 600 may include input devices, such as a keyboard, keypad, mouse, microphone, touch input device, touch screen, tablet, and/or the like. Such input devices may be coupled to the computing device 600 by wired or wireless connections including RF, infrared, serial, parallel, Bluetooth, Bluetooth low energy, USB, or other suitable connection protocols using wireless or physical connections. Similarly, the computing device 600 may also include output devices such as a display, speakers, printer, etc. Since these devices are well known in the art, they are not illustrated or described further herein.

While illustrative embodiments have been illustrated and described, it will be appreciated that various changes can be made therein without departing from the spirit and scope of the invention.

The embodiments of the invention in which an exclusive property or privilege is claimed are defined as follows:

1. A system for measuring blood flow during cardiopulmonary resuscitation of a subject, the system comprising:
    a blood flow sensor device that includes an ultrasound sensor;
    a gating signal generation device; and
    a blood flow monitoring computing device that includes at least one processor and a non- transitory computer-readable medium having computer-executable instructions stored thereon that, in response to execution by the at least one processor, cause the blood flow monitoring computing device to perform actions comprising:
        receiving blood flow information from the blood flow sensor device, wherein the blood flow information includes measurements of motion of blood within a blood vessel detected by the ultrasound sensor during cardiopulmonary resuscitation;
        receiving gating information from the gating signal generation device;
        determining time periods for sampling the blood flow information based on the gating information, wherein the time periods represent inter-compression events of the cardiopulmonary resuscitation;
        measuring blood flow indicated by the blood flow information during the time periods while ignoring blood flow indicated by the blood flow information outside of the time periods; and
        transmitting a command to a chest compression device based on the measured blood flow indicated by the blood flow information during the time periods, wherein the command includes at least one of an instruction to change a compression rate, an instruction to change a compression depth, and an instruction to change a compression duty cycle;
    wherein determining the time periods for sampling the blood flow information based on the gating information includes:
        detecting, based on the gating information, the inter-compression events of the cardiopulmonary resuscitation; and
        determining the time periods for sampling the blood flow information based on the detected inter-compression events;
    wherein receiving the gating information from the gating signal generation device and detecting the inter-compression events of the cardiopulmonary resuscitation includes at least one of:
        receiving tissue perfusion information from a photoplethysmography device and detecting minima of the tissue perfusion information;
        receiving motion information from a motion sensing device and using the motion information to detect the inter-compression events;
        receiving signals from a chest compression device indicating compression timing and using the signals indicating the chest compression timing to detect the inter-compression events; or
        receiving signals from a blood flow information filter device and detecting motion based on tissue-related backscatter signals indicated by the signals from the blood flow information filter device; and
    wherein measuring the blood flow indicated by the blood flow information during the time periods includes filtering, by the computing device, the blood flow information using a high-pass filter to screen out slow and bright tissue-related backscatter signals.

2. The system of claim 1, wherein the blood flow sensor device includes a non-imaging ultrasound probe.

3. The system of claim 2, wherein the blood flow sensor device includes an adhesive pad to affix the non-imaging ultrasound probe to the subject.

4. The system of claim 1, wherein the gating signal generation device is a photoplethysmograph device or an end tidal CO2 measurement device.

5. The system of claim 1, wherein the gating signal generation device is a motion sensing device.

6. The system of claim 1, wherein the system includes the chest compression device.

7. The system of claim 6, wherein the gating signal generation device is included within the chest compression device, and wherein the gating information indicates timing of operation of the chest compression device.

8. A computer-implemented method of measuring blood flow during cardiopulmonary resuscitation of a subject, the method comprising:
    receiving, by a computing device, blood flow information from a blood flow sensor device, wherein the blood flow sensor device includes an ultrasound sensor, and wherein the blood flow information includes measurements of motion of blood within a blood vessel detected by the ultrasound sensor during cardiopulmonary resuscitation;
    receiving, by the computing device, gating information from a gating signal generation device;
    determining, by the computing device, time periods for sampling the blood flow information based on the gating information, wherein the time periods represent inter-compression events of the cardiopulmonary resuscitation;
    measuring, by the computing device, blood flow indicated by the blood flow information during the time periods while ignoring blood flow indicated by the blood flow information outside of the time periods; and transmitting, by the computing device, a command to a chest compression device based on the measured blood flow indicated by the blood flow information during the time periods, wherein the command includes at least one of an instruction to change a compression rate, an instruction to change a compression depth, and an instruction to change a compression duty cycle;

wherein determining the time periods for sampling the blood flow information based on the gating information includes:
  detecting, based on the gating information, the inter-compression events of the cardiopulmonary resuscitation; and
  determining the time periods for sampling the blood flow information based on the detected inter-compression events;

wherein receiving the gating information from the gating signal generation device and detecting the inter-compression events of the cardiopulmonary resuscitation includes at least one of:
  receiving tissue perfusion information from a photoplethysmography device and detecting minima of the tissue perfusion information;
  receiving motion information from a motion sensing device and using the motion information to detect the inter-compression events;
  receiving signals from a chest compression device indicating compression timing and using the signals indicating the chest compression timing to detect the inter-compression events; or
  receiving signals from a blood flow information filter device and detecting motion based on tissue-related backscatter signals indicated by the signals from the blood flow information filter device; and wherein measuring the blood flow indicated by the blood flow information during the time periods includes filtering, by the computing device, the blood flow information using a high-pass filter to screen out slow and bright tissue-related backscatter signals.

9. The computer-implemented method of claim 8, wherein determining the time periods for sampling the blood flow information based on the detected inter-compression events includes, for each inter-compression event:
  determining a start time for the inter-compression event; and
  determining a time period that begins at the start time and ends a predetermined amount of time after the start time.

10. The computer-implemented method of claim 9, wherein the predetermined amount of time after the start time is about one-tenth of a second.

\* \* \* \* \*